United States Patent [19]

Kreuzman et al.

[11] Patent Number: 5,573,936
[45] Date of Patent: Nov. 12, 1996

[54] PROCESS FOR PURIFYING ECHINOCANDIN B DEACYLASE

[75] Inventors: Adam J. Kreuzman, Indianapolis; Wu-Kuang Yeh, Greenwood, both of Ind.

[73] Assignee: Eli Lilly and Company, Indianapolis, Ind.

[21] Appl. No.: 444,126

[22] Filed: May 18, 1995

Related U.S. Application Data

[62] Division of Ser. No. 534,394, Jun. 7, 1990.
[51] Int. Cl.$^6$ ............................................. C12N 9/16
[52] U.S. Cl. ........................... 435/196; 435/814; 435/815
[58] Field of Search ................................ 435/196, 814, 435/815

[56] References Cited

PUBLICATIONS

Boeck et al., Journal of Antibiotics 41(8), 1085–1092 (Aug. 1988).
Takeshima et al., Journal of Biochem. 105(4), 606–610 (Apr. 1989).

*Primary Examiner*—Michael G. Wityshyn
*Assistant Examiner*—Jon P. Weber
*Attorney, Agent, or Firm*—Ronald S. Maciak; Thomas G. Plant

[57] ABSTRACT

Echinocandin B deacylase is purified to near homogeneity from *Actinoplanes utahensis* by a process comprising, in order, extracting the soluble enzyme, heating to 60° C., hydrophobic interaction chromatography, $(NH_4)_2SO_4$ fractionation, gel filtration, cation exchange chromatography, dye-ligand chromatography, gel filtration, and cation-exchange chromatography.

1 Claim, No Drawings

PROCESS FOR PURIFYING ECHINOCANDIN B DEACYLASE

This application is a division of application Ser. No. 07/534,394 filed Jun. 7, 1990.

BACKGROUND OF THE INVENTION

This invention relates to enzyme technology. In particular it relates to a lipopeptide deacylase in purified form produced by the organism *Actinoplanes utahensis* which deacylates the lipophilic acyl side chains of the antifungal metabolites echinocandin B (ECB), aculeacin, and analogs of ECB.

Echinocandin B and aculeacin are known cyclic hexapeptides having the linoleoyl and palmitoyl side chains respectively. Boeck, L. D., et al., 1988. J. Antibiot. (Tokyo), 41, 1085–1092; Boeck, L. D., et al., 1989 J. Antibiot (Tokyo), 42, 382–388; and Kimura, Y., et al., 1987. Agri. Biol. Chem. 51, 1617–1623; report the deacylation of the linoleoyl group of ECB with whole cells of *Actinoplanes utahensis* and Pseudomonas species. Takeshima, H., et al., 1989. J. Biochem. 105, 606–610, report the purification and partial characterization of a deacylase from *A. utahensis* which deacylates aculeacin.

Structural modification of the natural antifungals has led to potentially useful therapeutic agents such as cilofungin and daptomycin. Debono, M., et al., 1989. J. Antibiot. (Tokyo), 42, 389–397; Debono, M., et al., 1988. Ann. N.Y. Acad. Sci. 544, 152–167; Gordee, R. S. et al., 1988. Ann. N.Y. Acad. Sci. 544, 294–309; and Boeck, L. D., et al., 1988. J. Antibiot. (Tokyo), 41, 1085–1092. For example, ECB has been deacylated with whole cells of *A. utahensis* to cleave the lipophilic acyl side chain to provide the cyclic hexapeptide nucleus of ECB. Reacylation of the nucleus by chemical means has provided the acyl ECB compounds such as cilofungin with improved antifungal properties.

Because of the need for improved antifungal agents for the treatment of systemic fungal infections methods for their production are important. Enzymatic methods for preparing such compounds are especially desirable since they are usually simpler and more economical methods than chemical methods. Accordingly the availability of enzymes useful for such conversions is highly desirable.

SUMMARY OF THE INVENTION

*Actinoplanes utahensis* deacylase is provided in purified form. The enzyme catalyzes the cleavage of the linoleoyl group of ECB and the palmitoyl group of aculeacin. The enzyme is a heterodimer comprising 63 KD and 18 KD subunits which is optimally active at pH 6.0 and 60° C. The enzyme is cell associated and is not affected by cofactors, metal ion chelators or sulfhydryl reagents.

The enzyme is useful in a method for the preparation of cyclic hexapeptide nuclei and in a method for the preparation of the cyclicpeptide nucleus of the A21978C antibiotics.

The invention also provides a method for purifying the deacylase enzyme to near homogeneity which comprises hydrophobic interaction, cation-exchange, dye-ligand chromatographies and gel filtrations.

DETAILED DESCRIPTION

The deacylase of *Actinoplanes utahensis* provided by this invention is referred to herein for convenience as ECB deacylase. The enzyme all of which is virtually cell-associated has the following physical, catalytic and kinetic properties in its purified state.

ECB deacylase is an 81-kilodalton (KD) heterodimer comprising 63-KD and 18 KD subunits. The amino-terminal sequences of the large and small subunits are respectively as follows.

Ser-Asn-Ala-Tyr-Gly-Leu-Gly-Ala-Gln-Ala-Thr-Val-Asn-Gly-Ser-Gly-Met-Val-Leu-Ala-Asn-Pro-His-Phe-Pro-(Trp)-Gln --- Ala-Glu-(Arg)-Phe-Tyr.

His-Asp-Gly-Gly-Tyr-Ala-Ala-Leu-Ile-Arg-Arg-Ala-Ser-Tyr-Gly-Val-(Pro)-His-Ile-Thr-Ala-Asp-Asp-Phe.

In the above sequences the amino acid residues in parentheses indicate a tentative assignment while "---" indicates that the residue has not as yet been identified.

The amino acid composition of the purified enzyme is shown below in Table I. The composition was determined by the method described by Dotzlaf, J. E. and Yeh, W-K, 1987. J. Bacteriol. 169, 1611–1618.

TABLE I

Amino Acid Composition of A. utahensis Deacylase

| Amino Acid | Number of Residues per 81,000-dalton |
| --- | --- |
| Asp + Asn | 74 |
| Thr | 51[a] |
| Ser | 83[a] |
| Glu + Gln | 45 |
| Pro | 42 |
| Gly | 85 |
| Ala | 79 |
| Cys | 10[b] |
| Val | 48 |
| Met | 5 |
| Ile | 25 |
| Leu | 53 |
| Tyr | 20 |
| Phe | 24 |
| His | 21 |
| Lys | 11 |
| Arg | 62 |
| Trp | 19[c] |

[a]Determined by extrapolation to zero time of hydrolysis.
[b]Determined by cysteic acid.
[c]Determined by hydrolysis in the presence of thioglycolic acid.

The molecular weight of ECB deacylase as estimated by gel filtration with Ultrogel AcA 44 was 46,000. The molecular weights of the subunits described above was determined by SDS-PAGE. The molecular weight determined by gel filtration is a significant underestimate that can be attributed to an abnormal gel elution behavior of the enzyme. The abnormal elution behavior of the enzyme on gel is typical of a membrane-bound protein attributable to the usually high hydrophobicity of the macromolecule.

ECB deacylase is a simple enzyme (although containing two subunits) that does not require any exogenous phospholipid, cofactor, metal ion or reducing agent for expression of its activity. Further, none of the common cofactors, metal ions or reducing agents stimulate the deacylase. Surprisingly, N-ethylmaleimide (NEM) enhances the rate of conversion of ECB to ECB nucleus about 6–7 fold and the purified deacylase.

An important property of the purified deacylase is its enhanced activity in the presence of high salt concentrations. The activity is increased by up to 3-fold in the presence of several common mono- and divalent metal salts. Salts such as sodium chloride, potassium chloride, magnesium chloride, calcium chloride, sodium or potassium nitrate are among such stimulatory salts. A preferred salt for this purpose is potassium chloride. Salt concentrations of about 0.1 molar up to about 3.0 molar appear to be the most favorable. Enhanced activity is observed at lower salt concentrations.

The lack of resolution observed for the deacylase by native-PAGE at pH 7 and 9 indicates that the isoelectric point of the enzyme is above 9. The native-PAGE was performed according to Blackshear, P. J. (1984) Methods Enzymol. 104, 237–255.

The substrate employed for study of the kinetic and catalytic properties of the purified enzyme was echinocandin B (ECB). ECB is essentially insoluble in aqueous solutions. Among several water miscible solvents tested for solubilization of ECB in aqueous media, dimethylsulfoxide (DMSO) at a low concentration of about 15% or lower was most compatible with the deacylase catalyzed reaction and subsequent enzyme activity analysis of HPLC.

The enzyme is optimally active at pH 6.0 at 60° C. in 0.05M $KH_2PO_4$ buffer. It was found that the enzyme was at least twice as active when the reaction (ECB to ECB nucleus) was initiated with the enzyme rather than with the substrate.

The Km of the deacylase for echinocandin B, as determined by the Lineweaver-Burk method, was 50 μM.

The Vmax for the ECB reaction was 10–11 μmol of the peptide (ECB nucleus) formed/min/mg protein.

Regarding the reaction stoichiometry, the ratio of ECB nucleus formed to ECB disappearance was observed to be about 52.4%. The low ratio of conversion observed may be attributable to the occurrence of some other reaction or possibly to some degradation.

As was noted hereinabove the *A. utahensis* deacylase is cell-associated. For example, in a typical 90-hour culture broth of *A. utahensis* that exhibits a high total activity of ECB deacylase, over 99% of the deacylase activity was cell-associated. Less than 5% of the cell-associated deacylase activity was released by incubation of the cells in 0.01M $KH_2PO_4$, pH 6.0 for one day. Increase of the ionic strength of this and other buffers had only a slight effect in recovery of a soluble deacylase. However it has been found that by treating the cells with salts such as potassium or sodium chloride, potassium or sodium nitrate and magnesium or calcium salts, a high recovery (60 to 80%) of soluble deacylase is realized. The effect of this salt-treatment is shown in Table II below.

TABLE II

Solubilization of ECB Deacylase From A. Utahensis

| Cell Treatment[a] | Activity Distribution (%) | Specific Activity (U/mg protein) |
|---|---|---|
| KCl/$KH_2PO_4$ and Sonication | | |
| Supernatant Fraction | 80 | 0.1 |
| Pellet Fraction | 20 | — |
| KCl/$KH_2PO_4$ Only | | |
| Supernatant Fraction | 60–80 | 0.2–0.4 |
| Pellet Fraction | 20–40 | — |
| $KH_2PO_4$ and Sonication | | |
| Supernatant Fraction | 80 | 0.1 |
| Pellet Fraction | 20 | — |
| $KH_2PO_4$ Only | | |
| Supernatant Fraction | 0 | — |
| Pellet Fraction | 100 | — |

[a] A. utahensis cells were resuspended in 0.8M KCl/0.05M $KH_2PO_4$ or 0.05M $KH_2PO_4$ only, pH 6.0, sonicated continually for one minute, wherever specified, and centrifuted at 48,000 × g for one hour.

The ECB deacylase is produced by culturing *Actinoplanes utahensis* under submerged aerobic fermentation conditions. The fermentation method and the conditions employed are known, Boeck, L. D., Fukuda, D. S., Abbott, B. J. and Debono, M., 1989. J. Antibiot. (Tokyo), 42, 382–388. Maximum production of the deacylase activity occurs at about 90 hours after inoculation of the culture medium. As described above and in Example 1 hereinafter the enzyme in crude form is solubilized by salt treatment of the whole cells preferably with potassium chloride.

The crude solubilized enzyme is purified to near homogeneity in the purification process of the invention which comprises hydrophobic interaction chromatography, cation-exchange chromatography and gel filtration steps. As described above herein the ECB deacylase behaves as a loosely cell-bound protein and is solubilized differentially by treating whole cells of *A. utahensis* with an inorganic salt. Preferably potassium chloride is used. The solubilized enzyme solution is desirably filtered and the filtrate concentrated by ultrafiltration to provide a more concentrated deacylase solution for the ensuing steps.

In the first step of the process the concentrated cell extract is heated for one hour at about 60° C. and is treated while warm with ammonium sulfate, 14%, and potassium chloride, 1.2M. The heat treatment causes other proteins in the solution which are unstable at 60° C. to precipitate. The ECB deacylase is stable at 60° C. and remains solubilized.

The heat treated extract is then subjected to hydrophobic interaction chromatography at a temperature of about 25° C. on a hydrophobic interaction chromatographic material such as lipid substituted agarose for example the commercially available Octyl Sepharose which is n-octyl coupled to highly cross-linked, spherical, 4% agarose beads (Pharmacia). The column is equilibrated to pH 6 with about 0.05M potassium dihydrogen phosphate or other suitable buffer, 1.2M potassium chloride and 14% ammonium sulfate. The column is desirably washed with the same buffer and the bound protein is eluted with a simultaneous linear gradient of KCl (1.2–0.1M) and $(NH_4)_2SO_4$ (14–0%) in 0.05M $KH_2PO_4$, pH 6 buffer. The ECB deacylase is eluted as a single, unsymmetrical activity peak.

The peak fractions containing about 95% of the total deacylase activity are pooled and subjected to ammonium sulfate fractionation. The 10–36% $(NH_4)_2SO_4$ fraction is collected and subjected to gel filtration in pH 6 buffer containing 0.8M KCl. Gel types which can be used may vary however Sephacryl S-200 HR, which is a spherical gel filtration medium prepared from allyl dextran and N,N'-methylene bisacrylamide, having particle size 25–75 μm, is a suitable gel. The enzyme is eluted as one main activity peak and a minor activity peak. The peak fractions which contain 90% of the deacylase activity from the main peak are pooled and adjusted to 0.05M KCl at pH 5.6. The pooled fractions are subjected to cation-exchange chromatography over a suitable cation-exchange resin such as one of the commercially available Trisacryl resins for example, Trisacryl-CM, which is a carboxymethyl cation exchange chromatography media on a beaded copolymer of acrylic acid and N-acryloyl-2-amino-2-hydroxymethyl- 1,3-propanediol (IBF Biotechnics). The column is equilibrated with 0.05M $KH_2PO_4$, pH 5.6, and 0.05M KCl. The column is washed with the same buffer and the bound proteins are eluted with a linear gradient of KCl (0.05M–0.5M) in the same buffer. The deacylase enzyme is eluted as two activity peaks.

The fractions containing the deacylase activity from each of the peaks are pooled, adjusted to 0.05M KCl, and applied to a dye-ligand gel such as Red-Sepharose, which is the dye-ligand, Procion Red, covalently coupled to highly cross-linked, spherical, 6% agarose beads (Pharmacia, Inc.) or Dyematrex Blue A, which is the dye ligand, Cibacron Blue 3GA, coupled to a support matrix (Amicon). The gel is equilibrated prior to use with 0.05M $KH_2PO_4$, pH 6.0, and 0.05M KCl. The bound proteins are eluted preferably with a step-wise gradient of KCl (0.05-2-3.3M) in the same buffer from the Red-Sepharose or preferably with a linear gradient of KCl (0.05–2.5M) in the same buffer from the Blue A gel. A broad and unsymmetrical activity peak is obtained from the dye-ligand chromatography.

The peak fractions containing about 80% of the total activity from the dye-ligand gel are pooled and subjected to gel filtration over a gel of the type such as Ultragel AcA 44, which is a gel filtration medium prepared from polyacrylimide and agarose gel (IBF Biotechnics) previously equilibrated with 0.05M $KH_2PO_4$, pH 6.0, and 0.2M KCl. The enzyme is eluted as a single activity peak and the peak fractions containing all of the deacylase are pooled.

The pooled fractions are adjusted to 0.04M KCl at pH 7.0 and then again subjected to cation exchange chromatography over a negatively charged resin such as Trisacryl-CM. The resin is equilibrated prior to use with 0.05M $KH_2PO_4$, pH 7.0, and 0.04M KCl buffer and bound deacylase is eluted with a step-wise gradient of KCl (0.04–0.5–2M) in the same buffer. One broad activity peak and one sharp minor activity peak are observed. The fractions from these two activity peaks of the purified enzyme can be stored at −70° C. for further use.

During the foregoing 8-step process for the purification of ECB deacylase two size-forms and two charge-forms of the enzyme are observed. The major peak obtained with the last cation-exchange chromatography was analyzed by SDS-PAGE and showed two closely slow-moving bands and two closely fast-moving bands. The minor cation-exchange chromatography peak showed a single slow-moving band and two fast-moving bands. The absence of the second slow-moving band suggests that this protein is likely a degradation product from the first slow-moving band.

The purified ECB deacylase provided by the purification process of the invention is useful in a method for deacylating lipo cyclicpeptides to provide the cyclicpeptide nuclei thereof. In particular the enzyme deacylates the cyclohexapeptides echinocandin B and aculeacin. Further the purified enzyme cleaves the fatty acid side chain from the cyclicpeptide A21978 antibiotic factors including Daptomycin.

The process of this invention comprises mixing at a temperature between about 25° C. and 75° C. in an aqueous medium at a pH between about 5 and about 7 a cyclicpeptide represented by the formula A or B

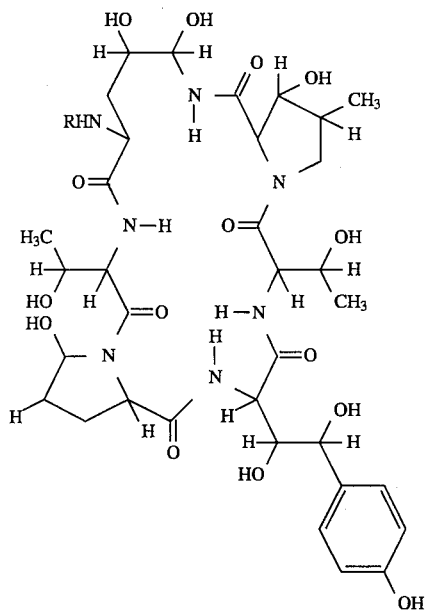

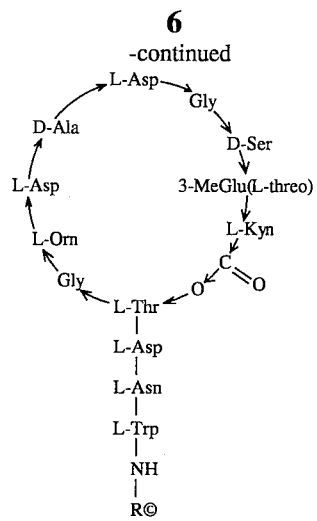

with echinocandin B deacylase where, in formula A, R is linoleoyl, myristoyl or palmitoyl and, in formula B, R' is decanoyl, 8-methyldecanoyl, 10-methylundecanoyl, or 10-methyldodecanoyl; to provide the compound of the formula A or B wherein R and R' are hydrogen.

The process is preferably carried out at a temperature between about 55° C. and about 65° C. The pH of the medium can be maintained with a suitable buffer. A salt such as an alkali metal chloride eg. KCl or NaCl or an alkali metal nitrate eg, $KNO_3$ appears to have a beneficial effect on the activity of the enzyme and can be incorporated in the aqueous medium. Preferably the salt is KCl at a concentration of about 0.05M to about 3.0M.

A water miscible solvent also can be added to the medium in the instance where the substrate's water solubility is low. For example, echinocandin B has a low solubility in water. Dimethylsulfoxide (DMSO) can be added to the reaction medium to enhance its solubility. DMSO is also compatible with the deacylase. In general DMSO can be added in amounts between about 5% and 15% v:v. as demonstrated in the case of ECB and aculeacin.

The process is preferably carried out by forming a solution of the substrate in the buffered aqueous medium, warming the mixture to the reaction temperature and adding the enzyme. The reaction mixture is stirred, shaken or otherwise agitated to provide good contact of substrate and enzyme. The reaction mixture can be monitored from time to time by assaying small aliquots of the mixture by the assay method described hereinafter. Alternatively, the solution of the substrate can be added to the buffered enzyme solution. However, better deacylation results are generally obtained by adding the enzyme to the substrate.

If, as determined by monitoring the reaction, the reaction is proceeding too slowly or has terminated prematurely additional fresh enzyme can be added to complete the deacylation.

The process also may be carried out with an immobilized form of the enzyme. The enzyme may be bonded to a suitable inert resin support and packed into a column. The aqueous buffered solution can be applied to the column and washed through with buffer. Recycling may be required to achieve complete conversion.

A preferred embodiment of the process of the invention comprises the deacylation of echinocandin B (formula A, R=linoleoyl) to the echinocandin B nucleus (formula A, R=H). Another preferred embodiment comprises the deacylation of aculeacin (formula A, R=palmitoyl) to the same ECB nucleus.

The substrate specificity studies carried out with the purified deacylase of the invention revealed rather broad specificity for the cyclicpeptides of the echinocandin B type formula A and the A21978 antibiotic type of formula B. The A21978 substrates are known metabolites described by U.S. Pat. No. 4,537,717. Also found to be substrates for the deacylase are certain derivatives of the ECB nucleus which are prepared by the acylation of the nucleus. Examples of such acyl derivatives are represented by the above formula A when R is a 3-phenylpropionyl group substituted in the para position by $C_7H_{15}O$-(30%), $C_5H_{11}O$-(12%); a phenylacetyl group substituted in the para position by $C_8H_7O$- (30%) or a $C_{11}H_{23}C(O)NH$-group (5%); a benzoyl group substituted in the para position by a $C_{11}H_{23}C(O)NH$-group; or a cinnamoyl group substituted in the para position by a $C_{11}H_{23}C(O)NH$-group (15%). The figures in parentheses are the percent activity relative to the deacylase activity of 100% for ECB itself.

The following example further illustrates and describes the invention but is not intended to be limiting thereof.

EXAMPLE 1

Preparation and Purification of ECB Deacylase

A. Fermentation of *Actinoplanes utahensis*

*Actinoplanes utahensis* NRRL 12052 was grown in a 150-liter fermenter under the conditions described by Boeck, L. D., Fukuda, D. S., Abbott, B. J., and Debono, M. 1989. J. Antibiot. (Tokyo), 42, 382–388. Cells containing a high activity of echinocandin B deacylase (90 hours after inoculation) were harvested by centrifugation; washed with 0.05M $KH_2PO_4$, pH 6.0, and used for enzyme isolation and purification.

B. Enzyme Solubilization and Purification

Unless otherwise specified the following isolation and purification procedures were carried out at a temperature between about 0° C. and 4° C.

Assay of 100 liters of fermentation medium at 90 hours showed that virtually all of the deacylase activity was cell-associated. The assay method employed throughout this example is described hereinafter.

Fresh cells (7.9 kg wet weight) were re-suspended in 0.05M $KH_2PO_4$, pH 6.0, with 0.8M KCl to a total volume of 57 liters and the suspension was stirred continuously for one day. Most of the cell-associated deacylase activity became soluble differentially by this salt treatment.

The solubilized deacylase was filtered through Whatman No. 1 paper and the filtrate was concentrated to a volume of 3.3 liters with an Amicon YM 30 spiral ultrafiltration cartridge. The concentrated extract was heated at 60° C. for one hour.

The heat-treated enzyme extract was treated with $(NH_4)_2SO_4$ at 14% concentration and KCl at 1.2M and was loaded onto a Octyl-Sepharose column (5×36 cm) previously equilibrated with 0.05M $KH_2PO_4$, pH 6.0, 1.2M KCl and 14% $(NH_4)_2SO_4$. The column was washed with two bed volumes of the same buffer and bound proteins were eluted with a simultaneous linear gradient of KCl (1.2–0.1M) and $(NH_4)_2SO_4$ (14–0%) in 0.05M $KH_2PO_4$, pH 6.0. This chromatography (hydrophobic interaction chromatography) was carried out at a temperature of about 25° C. ECB deacylase was eluted as a single but non-symmetrical activity peak.

The peak fractions containing 95% of the total deacylase activity were pooled and fractionated with $(NH_4)_2SO_4$. The 10–36% $(NH_4)_2SO_4$ fraction was loaded onto a Sephacryl S-200 HR column (5×69 cm) previously equilibrated with 0.05M $KH_2PO_4$, pH 6.0, and 0.8M KCl (buffer A). The deacylase was eluted as a main activity peak and a minor one. The peak fractions containing 90% of the enzyme activity from the main peak were pooled, adjusted to 0.05M KCl at pH 5.6 and were applied to a Trisacryl-CM column (2.5×33 cm) previously equilibrated with 0.05M $KH_2PO_4$, pH 5.6, and 0.05M KCl (buffer B). The column was washed with two-bed volumes of buffer B and bound proteins were eluted with a linear gradient of KCl (0.05–0.5M) in buffer B. The deacylase was eluted as two activity peaks.

The fractions containing the deacylase activity from each of the two peaks were pooled, one pool per peak. The two enzyme pools were adjusted to 0.05M KCl and one pool loaded onto a Red-Sepharose column (3.2×15.5 cm) and the other onto a Dyematrex Blue A column (2.2×22 cm). Both columns were previously equilibrated with 0.05M $KH_2PO_4$, pH 6.0, and 0.05M KCl (buffer C). After both columns were washed with two bed volumes of buffer C the bound protein was eluted from the Red-Sepharose column with a step-wise gradient of KCl (0.05–2–3.3M) in buffer C and from the Blue A column with a linear gradient of KCl (0.05–2.5M) in buffer C. A broad and non-symmetrical activity peak was observed from each dye-ligand chromatography.

The peak fractions containing 80% of the total deacylase activity from the Red-Sepharose peak were pooled and applied to a Ultragel Ac 44 column (1×118 cm) previously equilibrated with 0.05M $KH_2PO_4$, pH 6.0, and 0.2M KCl (buffer D). The deacylase was eluted as a single activity peak.

The peak fractions containing all of the deacylase activity were pooled, adjusted to 0.04M KCl at pH 7.0 and loaded onto a Trisacryl-CM column (1×34 cm) previously equilibrated with 0.05M $KH_2PO_4$, pH 7.0 and 0.04M KCl (buffer E). After the column was washed with two bed volumes of buffer E bound proteins were eluted with a step-wise gradient of KCl (0.04–0.5–2M) in buffer E. One broad main activity peak and one sharp minor activity peak were observed. The fractions from the two activity peaks were stored individually at −70° C. until required.

The following Table III shows the results obtained with each step of the isolation and purification of ECB deacylase detailed above.

TABLE III

Purification of ECB Deacylase

| Step | Protein (mg) | Activity (U) | Sp. Act. (U/mg) | Recovery (%) |
|---|---|---|---|---|
| Soluble Extract | 12,546 | 4,631 | 0.37 | 100 |
| Heat-Treated Extract (60° C. for 1-hr) | 7,325 | 3,606 | 0.49 | 78 |
| Octyl-Sepharose Eluate | 1,357 | 2,038 | 1.5 | 44 |

TABLE III-continued

Purification of ECB Deacylase

| Step | Protein (mg) | Activity (U) | Sp. Act. (U/mg) | Recovery (%) |
|---|---|---|---|---|
| 10–36% (NH$_4$)$_2$SO$_4$ Fraction | 1,077 | 1,513 | 1.41 | 33 |
| Sephacryl S-200 HR Eluate | 857 | 1,470 | 1.72 | 32 |
| Trisacryl-CM Eluate, pH 5.6 (A) | 78 | 293 | 3.76 | 6.3 |
| Trisacryl-CM Eluate, pH 5.6 (B) | 175 | 595 | 3.42 | 12.8 |
| Red-Sepharose Eluate (A1) | 10.1 | 58.4 | 5.78 | 1.3 |
| Blue A Eluate (B1) | 113 | 368 | 3.53 | 7.9 |
| Ultrogel AcA 44 Eluate (Ala) | 8.1 | 60.2 | 7.42 | 1.3 |
| Trisacryl-CM Eluate, pH 7.0 (Ala1) | 5.5 | 56.2 | 10.22 | 1.2 |
| Trisacryl-CM Eluate, pH 7.0 (Ala2) | 1.2 | 13.5 | 11.25 | 0.3 |

As described hereinabove, two activity peaks were observed in the first and second cation-exchange chromatography with Trisacryl-CM. The fractions from each of the two peaks A and B of the first chromatography were collected and analyzed separately as shown. The pooled A fractions were subjected to the Red-Sepharose dye-ligand chromatography (A1) while those of the second activity peak B were subjected to the Dyematrex Blue A dye-ligand chromatography (B1). When the eluates of each dye-ligand chromatography were analyzed the specific activity increased for the Red-Sepharose treatment while the specific activity for the Blue A increased only slightly. Accordingly, in this instance, the eluate of the Red-Sepharose column was selected for further purification by Ultrogel filtration (Ala) followed by cation-exchange chromatography with Trisacryl-CM. Again, as with the previous cation-exchange chromatography the two activity peaks (enzyme forms) were collected and analyzed separately.

Enzyme assay

The assay employed herein for determining and measuring deacylase activity utilizes echinocandin B as substrate. A typical reaction mixture of 1 ml for ECB deacylase assay contained 425 μmole of ECB and 0.000003 to 0.003 unit of the enzyme in 0.05M KH$_2$PO$_4$, pH 6.0, in the presence of 0.68M KCl and 15% DMSO to effect solution of the ECB. The enzymatic reaction was initiated by addition of the enzyme and was continued for 20 min at 60° C. before being interrupted by the addition of phosphoric acid. After a low-speed centrifugation to remove precipitated protein, the deacylase activity was determined by monitoring the formation of ECB nucleus at 225 nm using HPLC.

HPLC components were IBM PS/2 Model 80 and Color Display (IBM, Armonk, N.Y.), a Water 715 Ultra WISP Sample Processor (Waters Associates, Milford, Mass.), and a Beckman System Gold Programmable Solvent Module 126 and Scanning Detector Module 167 (Beckman, Fullerton, Calif.).

The ECB nucleus was eluted from an Apex Octadecyl 3 μ column (4.6×10 cm) (Jones Chromatography, Littleton, Co.) with a mobile phase of 3.9% CH$_3$CN/0.1% trifluoroacetic acid and a flow rate of 1 ml/min. The nucleus formation was linear with time during the assays. Duplicated HPLC analyses had an average 2–3% deviation. As used herein one unit of enzyme activity is defined as the amount of the deacylase required to cause formation of one μmole of the ECB nucleus per minute from ECB under the above described reaction conditions.

The specific activity (Table III) is defined as units per mg of protein. The protein content was determined by the method of Bradford using bovine serum albumin as standard (Bradford, M. M., (1976) Anal. Biochem. 72, 248–254.

We claim:

1. A process for preparing purified Echinocandin B deacylase, an enzyme that is a heterodimer of approximately 81-kilodaltons molecular weight; whose approximately 63-kilodalton subunit has the amino-terminal sequence: Ser-Asn-Ala-Tyr-Gly-Leu-Gly-Ala-Gln-Ala-Thr-Val-Asn-Gly-Ser-Gly-Met-Val-Leu-Ala-Asn-Pro-His-Phe-Pro; whose approximately 18-kilodalton subunit has the amino-terminal sequence: His-Asp-Gly-Gly-Tyr-Ala-Ala-Leu-Ile-Arg-Arg-Ala-Ser-Tyr-Gly-Val: and whose optimal catalytic activity for deacylation of echinochandin B is at about pH 6, at 60° C.; which comprises the steps;

(a) solubilizing the enzyme from *Actinoplanes utahensis* cells to produce a soluble extract;

(b) heating the soluble extract of step (a), buffered at about pH 6, for about one hour at a temperature of about 60° C.; and removing precipitate;

(c) adding to the heat-treated extract of step (b) (NH$_4$)$_2$SO$_4$ to a final concentration of about 14% (weight/volume) and KCl to a final concentration of about 1.2M KCl;

(d) loading the solution of step (c) onto a hydrophobic interaction chromatography resin equilibrated with pH 6 buffer containing about 14% (weight/volume) (NH$_4$)$_2$SO$_4$ and 1.2M KCl, and eluting bound ECB deacylase activity with a simultaneous linear gradient of KCl from 1.2 to 0.1M and (NH$_4$)$_2$SO$_4$ from 14 to 0% in pH 6 buffer, to produce a hydrophobic interaction eluate;

(e) adding to the hydrophobic interaction eluate of step (d) (NH$_4$)$_2$SO$_4$ to a concentration of about 10% of saturation, removing precipitate, adding (NH$_4$)$_2$SO$_4$ to a final concentration of about 36% of saturation, and recovering the precipitate to produce a 10–36% (NH$_4$)$_2$SO$_4$ precipitate;

(f) dissolving the 10–36% (NH$_4$)$_2$SO$_4$ precipitate of step (e) in pH 6 buffer containing 0.8M KCl, gel filtering the dissolved 10–36% (NH$_4$)$_2$SO$_4$ precipitate using a gel chromatography resin equilibrated with pH 6 buffer containing 0.8M KCl, and combining eluate containing deacylase activity;

(g) chromatographing the eluate of step (f) on cation-exchange chromatography resin equilibrated in pH 5.6 buffer containing 0.05M KCl, eluting a first and a second peak of deacylase activity from said cation-exchange chromatography resin using a linear gradient of KCl from 0.05M to 0.5M in pH 5.6 buffer, and combining cation-exchange chromatography eluate from the first peak containing deacylase activity;

(h) adjusting the KCl concentration of the combined elute of step (g) to about 0.05M, loading the combined eluate onto a dye-ligand chromatography resin, wherein the dye-ligand is Procion Red, equilibrated in pH 6 buffer containing 0.05M KCl, eluting said dye-ligand chromatography resin using a step-wise gradient of KCl from 0.05M to 2M to 3.3M, and combining eluate containing deacylase activity;

(i) gel filtering the dye-ligand chromatography eluate of step (h) using a gel chromatography resin equilibrated with pH 6 buffer containing 0.2M KCl;

(j) adjusting the KCl concentration of the gel filtration eluate of step (i) to about 0.04M KCl and about pH 7, chromatographing the gel filtration eluate using a cation-exchange chromatography resin equilibrated in pH 7 buffer containing 0.04M KCl, and eluting with successive steps of KCl concentration of 0.04M, 0.5M, and 2M; and (k) recovering purified Echinocandin B deacylase by combining eluate from the cation-exchange chromatography resin of step (j) containing deacylase activity.

* * * * *